(12) United States Patent
Panagiotopoulou et al.

(10) Patent No.: US 12,059,816 B2
(45) Date of Patent: Aug. 13, 2024

(54) APPARATUSES AND METHODS FOR MEASURING SKIN CHARACTERISTICS AND ENHANCING SHAVING EXPERIENCES

(71) Applicant: Bic Violex S.A., Anoixi (GR)

(72) Inventors: Vasiliki Panagiotopoulou, Athens (GR); Athanasia Panou, Athens (GR); Panagiotis Moustakas, Athens (GR); Georgios Pyrris, Athens (GR); Christos Galanis, Athens (GR); Georgios Goudelis, Athens (GR); Grigorios Gerasimos Koutsouridis, Salonika (GR); Paraskevi Aggelopoulou, Athens (GR)

(73) Assignee: BIC Violex Single Member S.A., Anoixi (GR)

( * ) Notice: Subject to any disclaimer, the term of this patent is extended or adjusted under 35 U.S.C. 154(b) by 1230 days.

(21) Appl. No.: 16/623,071

(22) PCT Filed: Jun. 1, 2018

(86) PCT No.: PCT/EP2018/064443
§ 371 (c)(1),
(2) Date: Dec. 16, 2019

(87) PCT Pub. No.: WO2019/011523
PCT Pub. Date: Jan. 17, 2019

(65) Prior Publication Data
US 2021/0146562 A1    May 20, 2021

Related U.S. Application Data

(60) Provisional application No. 62/532,534, filed on Jul. 14, 2017, provisional application No. 62/532,518, (Continued)

(51) Int. Cl.
  *B26B 21/40*    (2006.01)
  *A45D 44/00*    (2006.01)
  (Continued)

(52) U.S. Cl.
  CPC ............ *B26B 21/4056* (2013.01); *A61B 5/01* (2013.01); *A61B 5/0531* (2013.01);
  (Continued)

(58) Field of Classification Search
  CPC . B26B 21/4056; B26B 21/222; B26B 21/526; B26B 21/52; B26B 21/405;
  (Continued)

(56) References Cited

U.S. PATENT DOCUMENTS 4,205,441 A    6/1980  Turner
4,345,374 A    8/1982  Jacobson
(Continued)

FOREIGN PATENT DOCUMENTS

AU    2008216734 A1    8/2008
CN      201253862 Y    6/2009
(Continued)

OTHER PUBLICATIONS

Notice of Reasons of Refusal issued in corresponding Japanese Application No. 2022-116425, issued on Jun. 16, 2023.
(Continued)

*Primary Examiner* — Ghassem Alie
(74) *Attorney, Agent, or Firm* — Bookoff McAndrews, PLLC

(57) ABSTRACT

A shaving system comprising a handle, a cartridge including at least one blade, the cartridge being releasably coupled to the handle, a detector, at least one sensor coupled to at least one of the handle and the cartridge, wherein the at least one sensor is configured to output an electrical signal in response to an infrared thermal radiation, detected and measured by
(Continued)

the detector, of at least one skin property which is indicative of at least one skin characteristic, a processor configured to receive measurement data from the sensor and to at least one of identify and quantify the at least one skin characteristic based one the received measurement data, and a display configured to convey a message to the user based on skin characteristic data from the processor.

7 Claims, 9 Drawing Sheets

Related U.S. Application Data filed on Jul. 14, 2017, provisional application No. 62/532,682, filed on Jul. 14, 2017.

(51) Int. Cl.

| | | |
|---|---|---|
| *A61B 5/00* | (2006.01) | |
| *A61B 5/01* | (2006.01) | |
| *A61B 5/02* | (2006.01) | |
| *A61B 5/0205* | (2006.01) | |
| *A61B 5/0531* | (2021.01) | |
| *A61B 5/103* | (2006.01) | |
| *B26B 21/22* | (2006.01) | |
| *B26B 21/52* | (2006.01) | |
| *G01N 21/3563* | (2014.01) | |
| *G01N 27/04* | (2006.01) | |
| *G01N 33/483* | (2006.01) | |

(52) U.S. Cl.
CPC ............ *A61B 5/1032* (2013.01); *A61B 5/442* (2013.01); *A61B 5/6887* (2013.01); *A61B 5/742* (2013.01); *B26B 21/222* (2013.01); *B26B 21/4031* (2013.01); *B26B 21/526* (2013.01); *A45D 2044/007* (2013.01); *B26B 21/522* (2013.01)

(58) Field of Classification Search
CPC . B26B 21/4031; B26B 21/522; B26B 19/388; A61B 5/0531; A61B 5/6887; A61B 5/742; A61B 5/01; A61B 5/1032; A45D 2044/007
USPC ......................................................... 30/34.5
See application file for complete search history.

(56) References Cited

U.S. PATENT DOCUMENTS

| | | | |
|---|---|---|---|
| 7,100,283 B1* | 9/2006 | Grdodian .............. B26B 21/526 | |
| | | | 30/41.7 |
| 9,592,615 B1 | 3/2017 | Broeske | |
| 11,529,745 B2* | 12/2022 | Zafiropoulos ......... B26B 19/388 | |
| 2002/0088121 A1 | 7/2002 | Jacobsen | |
| 2012/0167392 A1 | 7/2012 | Cherian et al. | |
| 2013/0118326 A1* | 5/2013 | Ascari ...................... B26D 3/26 | |
| | | | 83/79 |
| 2015/0051845 A1* | 2/2015 | Alhashemi .......... B26B 21/4056 | |
| | | | 702/34 |
| 2016/0167241 A1 | 6/2016 | Goldfarb et al. | |
| 2017/0056685 A1* | 3/2017 | Harvey ................. A61B 5/443 | |
| 2017/0099199 A1 | 4/2017 | Bauer et al. | |
| 2018/0354147 A1* | 12/2018 | Goldfarb ............. B26B 21/4087 | |
| 2020/0033448 A1* | 1/2020 | Bourquin .............. G01S 7/4816 | |

FOREIGN PATENT DOCUMENTS

| | | | | |
|---|---|---|---|---|
| CN | 104010776 A | | 8/2014 | |
| CN | 203970406 U | * | 12/2014 | ........... A61N 5/0616 |
| CN | 203970406 U | | 12/2014 | |
| CN | 104379055 A | | 2/2015 | |
| CN | 204673652 U | | 9/2015 | |
| CN | 105705093 A | | 6/2016 | |
| EP | 362616 A | * | 4/1990 | ............. A61B 5/441 |
| GB | 2529999 A | | 3/2016 | |
| JP | H0438930 A | * | 2/1992 | ......... B26B 21/4056 |
| JP | H07204370 A | | 8/1995 | |
| JP | 2001029674 A | | 2/2001 | |
| JP | 2013512749 A | | 4/2013 | |
| JP | 2013528116 A | | 7/2013 | |
| JP | 2018182626 A | * | 11/2018 | ......... B26B 21/4056 |
| WO | WO 1995022444 A1 | | 8/1995 | |
| WO | WO 2004018161 A2 | * | 3/2004 | ........... B26B 21/222 |
| WO | 2011159790 A1 | | 12/2011 | |
| WO | 2011070486 A1 | | 6/2016 | |

OTHER PUBLICATIONS

Office Action issued in Japanese Patent Application No. 2019-572397, dated Apr. 15, 2022 (19 pages).
Office Action issued in Chinese Patent Application No. 201880042569.0, dated Oct. 9, 2021 (20 pages).
International Search Report and Written Opinion mailed on Nov. 26, 2018, in International Application No. PCT/EP2018/064423 (5 pages).
First Search issued in corresponding Chinese Application No. CN110785271A, issued on Mar. 19, 2021.

* cited by examiner

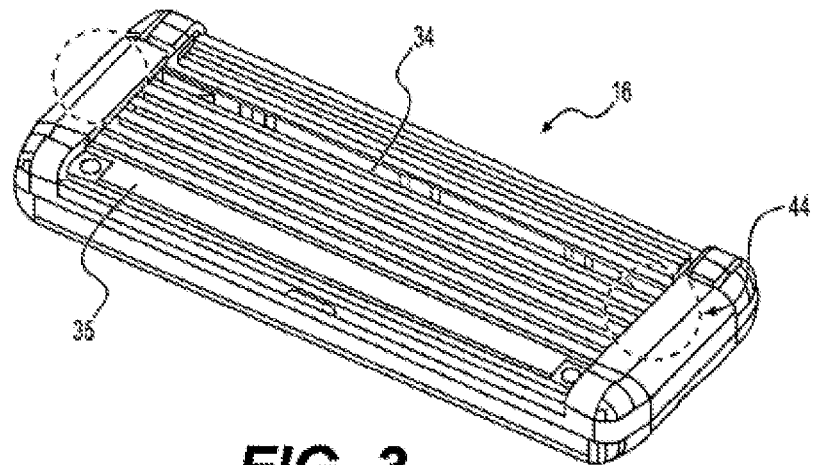
FIG. 3
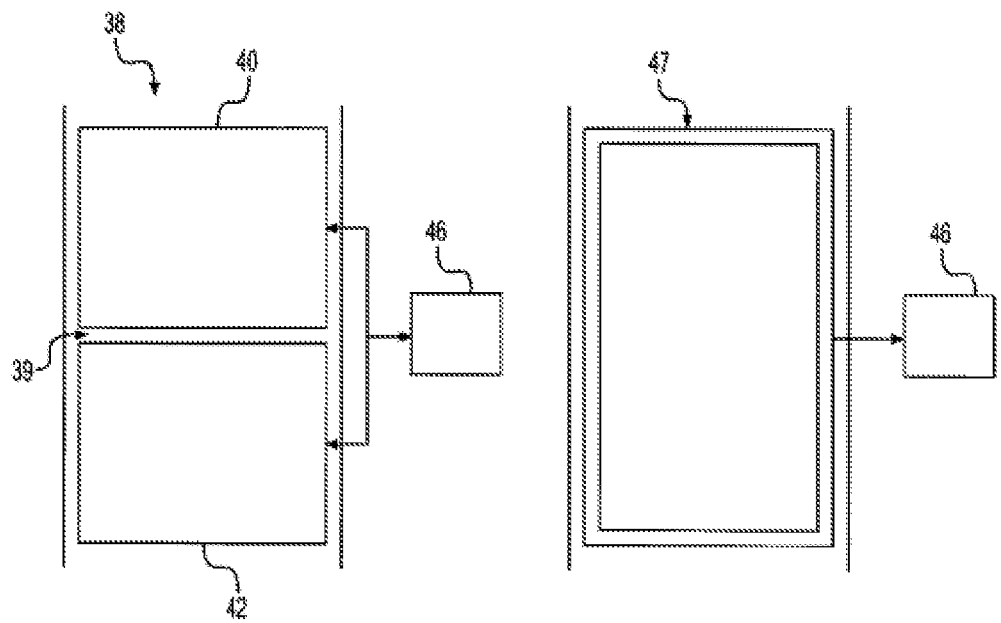
FIG. 4  FIG. 5

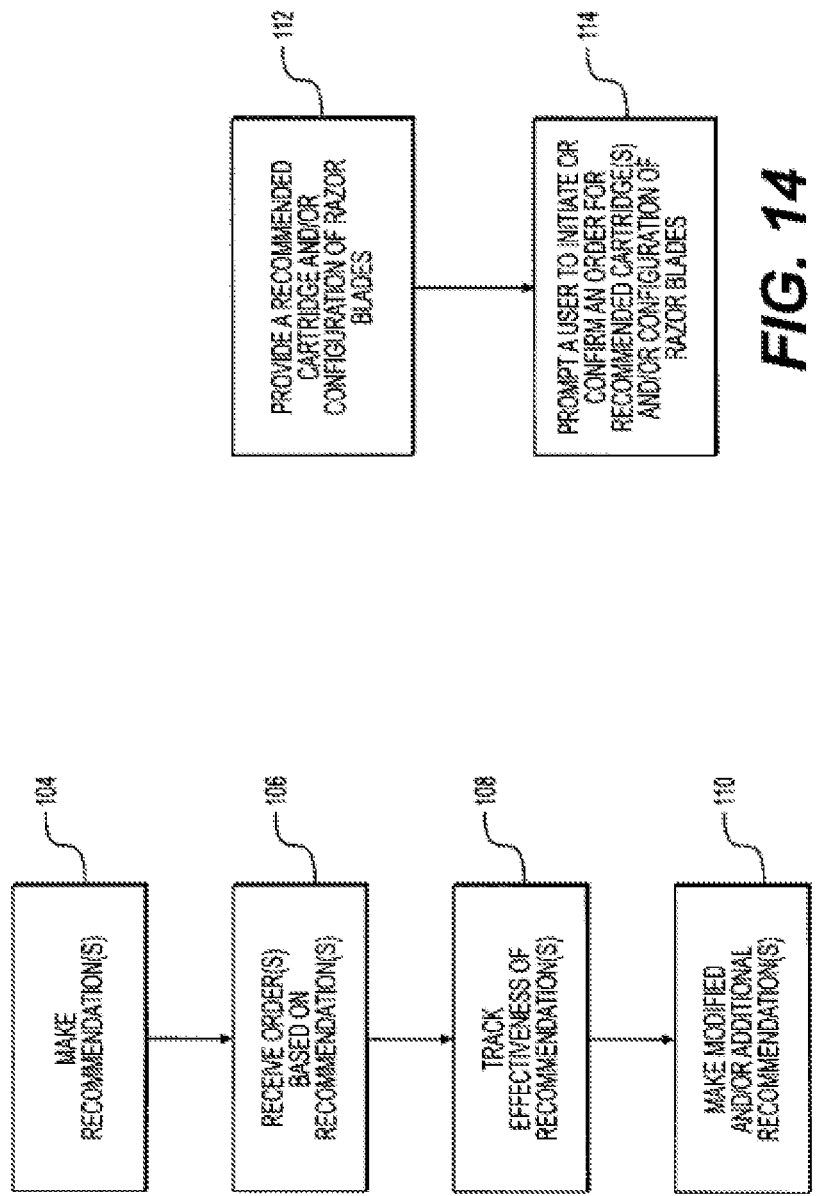

APPARATUSES AND METHODS FOR MEASURING SKIN CHARACTERISTICS AND ENHANCING SHAVING EXPERIENCES

CROSS-REFERENCE TO RELATED APPLICATIONS

This application is a National Stage Application of International Application No. PCT/EP2018/064443, filed on Jun. 1, 2018, now published as WO 2019/011523 A1, and which claims the benefit of U.S. Provisional Application Nos. 62/532,518, filed Jul. 14, 2017; 62/532,534, filed Jul. 14, 2017; and 62/532,682, filed Jul. 14, 2017.

TECHNICAL FIELD

Aspects of the present disclosure relate generally to shaving technology, and, specifically, to a shaving system and related methods for measuring one or more characteristics of a user's skin to determine the skin characteristics and/or skin elasticity, and/or for measuring irritation to the skin caused by shaving. Aspects of the present disclosure also relate generally to enhancing the shaving experience, and, specifically, to making recommendations to a user based on the skin characteristics determination, the skin elasticity determination, and/or the determined level of irritation.

DESCRIPTION OF RELATED TECHNOLOGY

Shavers generally include a handle and a razor cartridge releasably attached to one end of the handle. The razor cartridge includes at least one blade for cutting hairs. A user holds the handle and repeatedly moves the blade or blades across an area of the body to be shaved to cut the hairs on the area. Lubricating material may often be used to help hydrate and protect the user's skin during shaving. Insufficient or improper lubrication, inappropriate blade type or angle, and/or improper technique during shaving may result in skin irritation and/or nicks and cuts.

Generally, skin characteristics may vary from user to user and even across different portions of a user's body. Skin of differing characteristics may respond differently to various razor cartridge blade arrangements (e.g., blade angle or spacing). For example, certain skin characteristics having a low elasticity may experience a comfortable shave with a razor cartridge having a first number of blades spaced apart by a first distance. Other skin characteristics having a higher elasticity may experience a comfortable shave with a razor cartridge having a greater number of blades spaced relatively closer together. Having an understanding of this variability, and being able to make recommendations based on that understanding, may enhance a user's shaving experience.

BRIEF DESCRIPTION OF THE DRAWINGS

The accompanying drawings, which are incorporated in and constitute a part of this disclosure, illustrate various exemplary embodiments and together with the description, serve to explain the principles of the disclosure.

Aspects of the disclosure may be implemented in connection with embodiments illustrated in the attached drawings. These drawings show different aspects of the present disclosure and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure. There are many aspects and embodiments described herein. Those of ordinary skill in the art will readily recognize that the features of a particular aspect or embodiment may be used in conjunction with the features of any or all of the other aspects or embodiments described in this disclosure.

FIG. 3 depicts an exemplary razor cartridge, according to aspects of the present disclosure.

FIG. 4 depicts an exemplary sensor device, according to aspects of the present disclosure.

FIG. 5 depicts another exemplary sensor device, according to aspects of the present disclosure.

FIG. 13 depicts a flow diagram of a method for improving shaving sessions, according to aspects of the present disclosure.

FIG. 14 depicts a flow diagram of aspects of a method for improving shaving sessions, according to aspects of the present disclosure.

DETAILED DESCRIPTION

Figure 1:
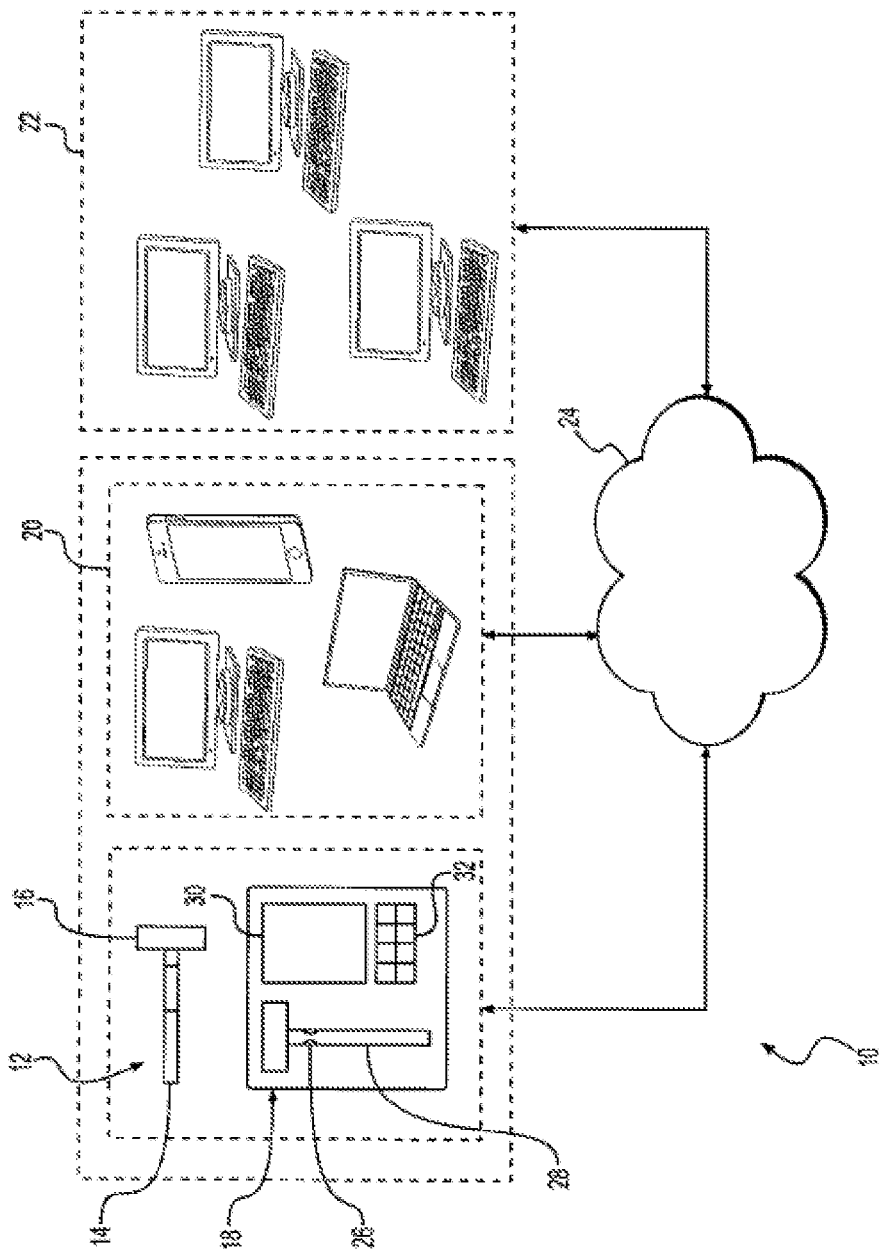
FIG. 1 depicts an exemplary shaving system, according to aspects of the present disclosure.

Examples of the present disclosure include systems, devices, and methods to facilitate and improve the experience of shaving. For example, aspects of the present disclosure may provide a user with the ability to measure, determine, or otherwise identify a feature or features of his or her skin and select a razor cartridge with features (e.g., a blade geometry or configuration) that is most appropriate for the user's skin based at least on the identified feature(s). More specifically, certain aspects of the present disclosure describe a shaver that includes one or more sensor devices for identifying skin conductance, skin elasticity, skin irritation, and/or other skin characteristics, and provide feedback and/or recommendations.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." It should be noted that all numeric values disclosed or claimed herein (including all disclosed values, limits, and ranges) may have a variation of +/−10% (unless a different variation is specified) from the disclosed numeric value. Moreover, in the claims, values, limits, and/or ranges means the value, limit, and/or range+/−10%. The terms "proximal" and "distal" are used herein to refer to the relative positions of the components of an exemplary device. When used herein, "proximal" refers to a position relatively closer to the portion of the device being held or otherwise handled by a user. In contrast, "distal" refers to a portion of the device in contact with a portion of the body being shaved. In the context of the exemplary shaver described herein, a distal portion of a device contacts the skin that is being shaved, whereas a proximal portion of the device is farther away from the skin that is being shaved and may be held by the user.

Reference will now be made in detail to the exemplary aspects of the present disclosure described below and illustrated in the accompanying drawings. Wherever possible, the same reference numbers will be used throughout the drawings to refer to same or like parts.

Additional objects and advantages of the disclosed aspects will be set forth in part in the description that follows, and in part will be readily apparent from the description, or may be learned by practice of the embodiments. It is to be understood that both the foregoing general description and the following detailed description are exemplary and explanatory only and are not restrictive of the claims.

Embodiments of the present disclosure may promote better shaving habits by creating a more efficient and enjoyable shaving session for a multitude of users by identifying each user's skin characteristics, skin elasticity, and/or skin irritation from shaving and, in some instances, providing a recommendation to the user based thereon.

A shaving system 10 is shown in FIG. 1. The system 10 may identify skin characteristics, skin elasticity, and/or skin irritation and facilitate and promote efficient shaving techniques for an improved shaving experience via, e.g., recommendations or other feedback provided to the user. The shaving system 10 may include a shaver 12 having a handle 14 and a razor cartridge 16 releasably attached thereto, a base 18, one or more user devices 20, and one or more merchant units 22. Each of the shaver 12, base 18, user device 20, and merchant unit 22 may be in operative communication with one or more of the other components. The communication may entail transmitting and receiving data signals through wired or wireless connections such as, for example, through a Bluetooth™ connection, AirDrop™, wired and/or wireless internet, and/or any other suitable connection 24. It also is contemplated that one or more of the shaver 12, base 18, user device 20, and merchant unit 22 may include one or more memory elements to store information, one or more processors to process information, and one or more power sources, such as a battery and/or an external plug for an outlet, to power electronic components and devices therein.

Figure 2:
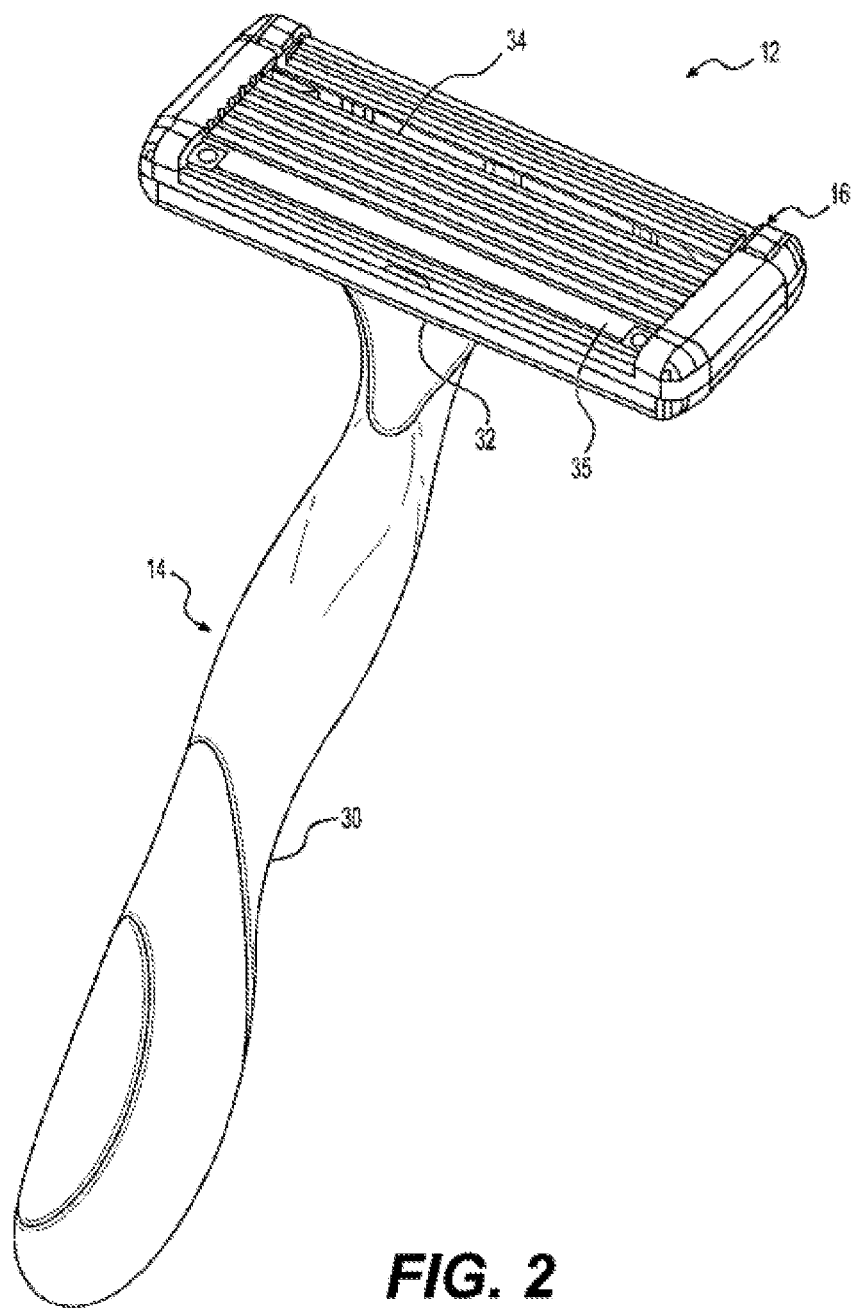
FIG. 2 depicts an exemplary shaver, according to aspects of the present disclosure.

As shown in FIG. 2, the handle 14 may include a handle body 30 configured to be held by a user. Handle body 30 may include any suitable configuration to promote comfortable gripping by a user. For example, the handle body 30 may include coatings or coverings such as, for example, a rubber covering, or may contain geometric features to prevent handle 14 from slipping within a hand of the user, especially when the handle 14 may be wet. The handle 14 also may include a handle attachment interface 32 at one end of the handle body 28. The handle attachment interface 32 may be configured to selectively attach and release cartridge 16 to/from handle 14 through any mechanism known for attaching and releasing a cartridge with a shaving handle. Additionally, the handle attachment interface 32 may be configured to couple to various types of razor cartridges 16. Although not shown, the handle 14 may further include one or more inputs, such as, for example, a button or switch, to activate, deactivate, and/or adjust operation of one or more electronic components, such as the one or more sensor devices described below.

The cartridge 16 may include a variety of different blade geometries and/or configurations. For example, the various blade geometries/configurations may include varying numbers of razor blades 34. The various blade geometries and/or configurations may also include different spacing distances between adjacent razor blades. The space between adjacent razor blades may be referred to as the Inter Blade Span (IBS), for example. In one example, the cartridge 16 may include at least two razor blades 34, at least three razor blades 34, at least four razor blades 34, or at least five razor blades 34. The cartridge 16 may include a plurality of razor blades 34 with an IBS between approximately 0.4 mm and approximately 1.8 mm. Any of the razor blades 34 in any of the above discussed examples of the cartridge 16 may include different blade spacings, blade thicknesses, blade angles, and/or antifriction blade coatings. The cartridge 16 may include different types of razor blades 34, e.g., fixed blades, movable blades, bent blades, etc. The cartridge 16 may include a moisturizing strip 35 and/or other comfort enhancing features adjacent to razor blades 34. Although not shown, cartridge 16 may include a trimmer blade as well. The cartridge 16 may also include a handle coupling portion (not shown) configured to releasably engage the handle attachment interface 32, such that the cartridge 16 may be selectively coupled to and released from the handle 14.

The handle 14 of shaver 12 may be removably coupled to the base 18 by, for example, a snap-fit, latching, or locking mechanism 26 (FIG. 1) that removably secures the handle 14 to the base 18 between uses, during travel, or during shipment from a merchant or manufacturer. Additionally or alternatively, any other portion of shaver 12 may be removably coupled to base 18, including the cartridge 16. Furthermore, the base 18 may include a mount or cradle 28, which may include either a wired or wireless charging apparatus (e.g., electrodes or an inductive coil) for any electronic elements in the handle 14, the cartridge 16, and/or in any other portion of the shaver 12. The locking mechanism 26 may retain the shaver 12 in the cradle 28.

The base 18 also may include a display 30. The display 30 may be any suitable display, including but not limited to, a liquid crystal display (LCD) unit. The display 30 may visually or graphically display information to the user, for example, user information, recommendations for the shaver 12, feedback or other educational or informative content, and/or shaving or other usage suggestions. The displayed information may be based on the data or information received from the shaver 12 or otherwise received from the user, e.g., via manual user input. Alternatively or additionally, the base 18 may audibly provide information to the user via a speaker.

The base 18 may solicit or otherwise request input or feedback from a user via, e.g., the display 30. For example, information may be displayed during, before, or after a shave session, or in response to a user input, in the form of prompts. An input 32 may allow a user to respond to prompts displayed on the display 30. Though only one input 32 is depicted, the base 18 may include more than one input 32. Input 32 may be touch sensitive and/or may include voice-activation technology so that a user may speak commands to the base 18.

In one aspect, any one or all of the features discussed above with respect to the base 18 may be incorporated into one or both of the handle 14 or the user device 20. For example, although not shown, the handle 14 may further include a display and/or user input buttons or switches. In some aspects, all of the functionality provided by base 18 may be incorporated into the shaver 12, for example, into the handle 14, and base 18 may be omitted altogether. In such aspects, the shaver 12 may be configured to directly transmit to and receive information from the user device 20.

Although not shown, the base 18 may further include a transceiver configured to transmit and/or receive data or other signals to and from the shaver 12, the user devices 20, and/or the merchant units 22. The transceiver may exchange electronic information with the other elements via the connection 24. Additionally, the base 18 may include a memory to store information related to the shaver 12 (including, e.g., information on any sensor devices therein), the cartridge 16, the razor blades 34, and/or user input information. The base 18 may include a power source, or may be configured to be coupled to a household electrical socket providing electrical energy between 110V-260V.

The aforementioned elements of the base 18 may be electronically connected such that information received and/or processed may be displayed and/or transmitted to the user devices 20 and/or merchant units 22, and also stored or accessed via the memory. In some aspects, the base 18 may include a wireless antenna charging connection such that the base 18 may charge the electronic elements in the shaver 12 (e.g., electronic elements in the handle 14 and/or in the cartridge 16) when the shaver 12 is placed on the handle mount 28. If the handle connection is wired, the base 18 may include a cable output of a specific voltage level appropriate for recharging the batteries of the electronic elements in the shaver 12. Alternatively, the base 18 may include a cavity (not shown) and/or extension element (not shown) that includes charging pins (not shown) on which the shaver 12 may be placed such that the electronic elements may be recharged.

According to further aspects, the base 18 may solicit or otherwise request input or feedback from a user via, e.g., the display 30. For example, information may be displayed during, before, or after a shave session, or in response to a user input. The input(s) 32 may allow a user to respond to prompts displayed on the display 30, such as, for example, to confirm a blade configuration or an order operation. According to some aspects, the input(s) 32 may be touch sensitive, such as, for example, buttons. According to other aspects, however, the input(s) 32 may be replaced with voice-activation technology so that a user may speak commands to the base 18. As such, the base 18 also may include a speaker and microphone to provide and receive voice instructions. The input(s) 32 may also allow a user to modify the information displayed on the display 30, such as, for example, to input user information, to toggle information sets, to change settings, to reset a cartridge or blade configuration, or to adjust an order for cartridges or other user preferences. According to further aspects, the display 30 may be touch sensitive such that the user may respond to prompts and/or modify the information presented on the display 30 by touching the display 30. The input(s) 32 may also include a power switch to turn the electronic components of the base 18 (and/or electronic components of the shaver 12) on and off. In one aspect, one or more of the sensor devices below may be controlled via the one or more inputs 32. In another aspect, the handle 14 may include a similar input (not shown) for controlling one or more of the sensor devices.

The user device(s) 20 may include a smartphone, tablet, smartwatch, computer, or other device that may run a downloadable application or an application accessed via the Internet. The application may include, for example, a user interface for the system 10. The application may be configured to receive information from and send information to the other parts of system 10. The application may include one or more software elements to receive, process, and/or generate information. Any one or all of the features associated with the user device 20 may be incorporated into one or both of the shaver 12 (e.g., in the handle 14) of the base 18.

In one example, the mobile application may be configured to receive information from handle 14, cartridge 16, one or more sensor devices, base 18, and/or merchant units 22 through the connections between the user device 20 and the other elements of the system 10, or through the connection between the user device 20 and the Internet. The mobile application also may transmit information to the merchant unit 22 in order to provide user data, to place orders, etc. to the merchant unit. The mobile application may provide the same information and user interaction as discussed above with respect to the display 30 on the base 18.

Figure 6:
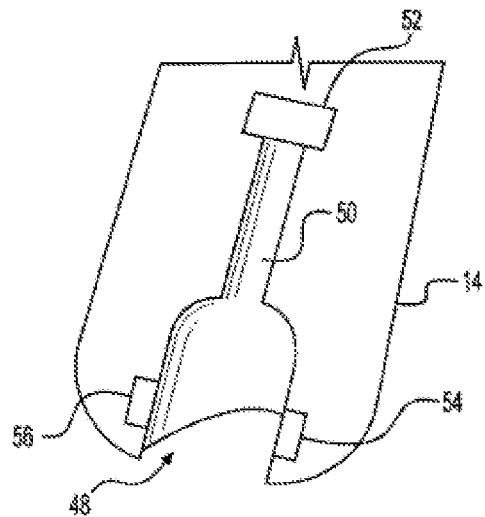
FIG. 6 depicts a cross-sectional view illustrating various aspects of an exemplary sensor device, according to aspects of the present disclosure.
Figure 7:
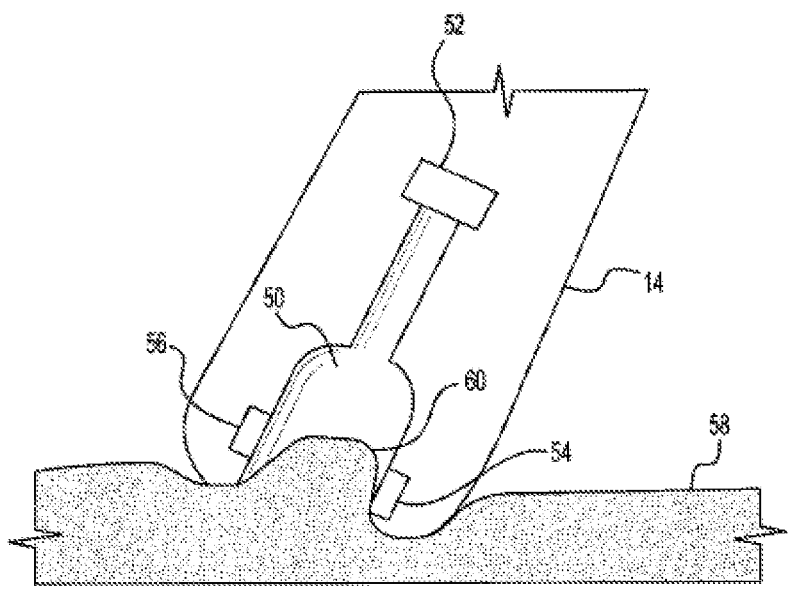
FIG. 7 depicts a cross-sectional view illustrating various aspects of an exemplary sensor device, according to aspects of the present disclosure.
Figure 8:
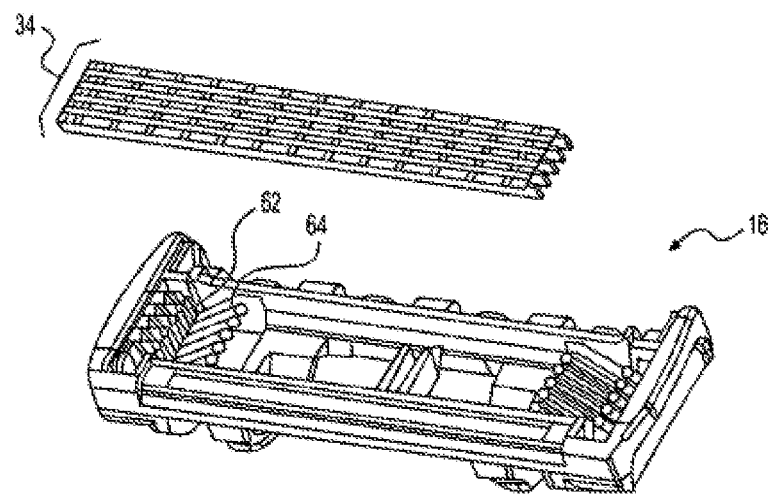
FIG. 8 depicts components of an exemplary razor cartridge in a disassembled state, according to aspects of the present disclosure.
Figure 9:
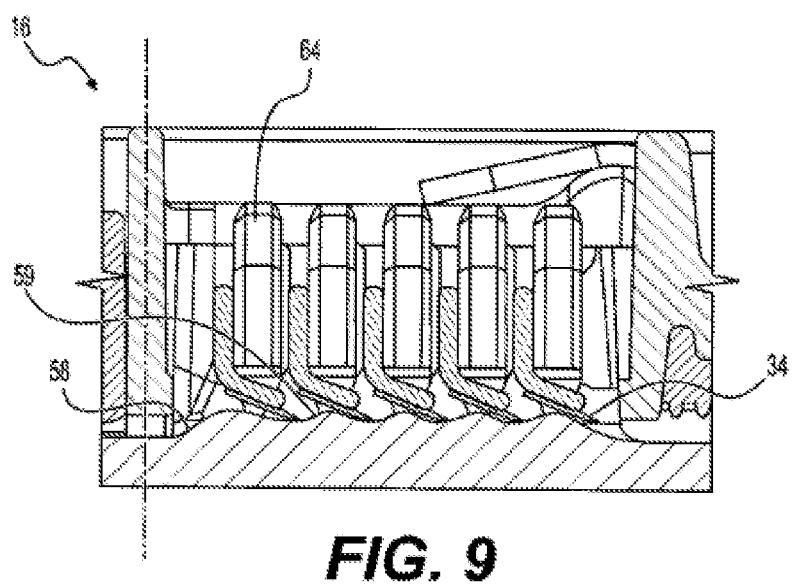
FIG. 9 depicts a cross-sectional view of a portion of the exemplary razor cartridge of FIG. 8, according to aspects of the present disclosure.

A close-up view of the shaver 12 is shown in FIG. 2. The shaver 12 includes the handle 14 and the razor cartridge 16, with the cartridge 16 having one or more razor blades 34 for cutting hair. A close-up view of the cartridge 16 is shown in FIG. 3, with even closer views of a surface of the cartridge 16 being shown in FIGS. 4 and 5. A close-up view of a proximal end of the handle 14 is shown in FIGS. 6 and 7. A partially disassembled view of the cartridge 16 is shown in FIG. 8, and a close-up cross-sectional view of a portion of the cartridge 16 is shown in FIG. 9.

The shaver 12 also may include one or more sensor devices. The sensor device may include any suitable sensors now know or developed in the future to identify skin characteristics, skin elasticity, and/or skin irritation caused by shaving. Examples of sensor devices are described in detail in the paragraphs below. The shaver 12 may include only a single sensor device. Alternatively, the shaver 12 may include a plurality of sensor devices. For example, the shaver 12 may include a grid or other arrangement of sensor devices that may take multiple measurements simultaneously and/or by different means. The sensor device(s) may be disposed on any suitable surface of the shaver 12 (e.g., on the handle 14 and/or the cartridge 16) that may be brought into contact with and/or faces a user's skin during a shaving session. Measurements may be made by the sensor device(s) once prior to and/or during a shaving session, repeatedly at one or more time intervals during a shaving session, or continuously during a shaving session or even after a shaving session.

In one example one or more sensor devices may be on the cartridge 16, such that the sensor devices may be brought into contact with the user's skin (see, e.g., FIGS. 4 and 5). Additionally or alternatively, one or more sensor devices may be one or within the handle 14 (see, e.g., FIGS. 6 and 7). Additionally or alternatively, on or more sensor devices may be housed within the cartridge 16 (see, e.g., FIGS. 8 and 9). The shaver 12 may include any of the sensor devices either alone or in combination with others. The paragraphs below outline exemplary aspects of the various forms of the sensor devices. It should be understood, however, that the aspects described with respect to a particular sensor device also may be applied to any of the other sensor devices.

In accordance with aspects of the present disclosure, one or more of the sensor devices may include a conductance sensor device 38 (FIG. 4). In one example, the conductance sensor device 38 may be configured to measure the conductance of portions of the user's skin when in contact with the conductance sensor device 38. The measured conductance of the portion of the user's skin may be an indicator of one or more physical characteristics of the portion of the user's skin, and accordingly, the user's skin characteristics may be identified based on the measured conductance. The conductance of the user's skin may be influenced by a multitude of factors. For example, the skin is composed of different layers having different characteristics from one person to another. When an external current is applied to the skin, the skin may act like an electrical network built of resistors and capacitors. Tissue, blood, and interstitial fluid in the skin may have differing conductance, dependent on their ionic concentration, and may act like variable resistors. Cellular boundaries formed by membranes in the skin may have more capacitor-like characteristics. The characteristics of these and other skin features may define the conductance of the skin, and qualities of those features may be different for different users. In some aspects, the contemplated external current may be applied via the conductance sensor device 38, e.g., the electrodes described below, or via the one or more of blades 34. For example, the electrodes described below may be provided on a single blade 34, or alternatively, a pair of electrodes may be provided on a pair of blades 34 (with one electrode on each of the blades 34). It also is contemplated that the blades 34 themselves may be the electrodes.

Aspects of an exemplary skin conductance sensor device 38 will now be described. In one example, the conductance sensor device 38 may be on the cartridge 16 (at, for example, regions enclosed by the dashed-line circles in FIG. 3), and may include a pair of electrodes 39 including a first electrode 40 and a second electrode 42 (see FIG. 4). The first and second electrodes 40 and 42 may be mounted on or embedded into a surface of the cartridge 16 that they may come into contact with the user's skin during use of the shaver 12. For example, the first and second electrodes 40 and 42 may be positioned around the periphery of the cartridge 16 at or adjacent the region of the cartridge 16 that contains the blades 34. The first and second electrodes 40 and 42 may be on opposite sides of the periphery. Alternatively, the first and second electrodes 40 and 42 may be on the same side of the periphery, but adequately separated so that an electrical current flowing between the first and second electrodes 40 and 42 must travel through the user's skin. For example, one or more of the described electrodes may be positioned on one or more clips 44 holding the blades 34 on the cartridge 16. The first and second electrodes 40 and 42 may protrude from portions of the surface of cartridge 16 on which they are positioned. Alternatively, the first and second electrodes 40 and 42 may be even with portions of the surface of the cartridge 16 on which they are positioned. Alternatively still, the first and second electrodes 40 and 42 may be recessed from the portions of the surface of cartridge 16 on which they are positioned, such that they may come into contact with the user's skin when a sufficient amount of pressure is applied to the user's skin by the cartridge 16. Alternatively, the first and second electrodes 40 and 42 may be on or formed by one or more of the blades 34.

The shaver 12 may include only a single conductance sensor device. Alternatively, the shaver 12 may include a plurality of conductance sensors. For example, the shaver 12 may include a grid of electrode pairs that may be positioned around the periphery of the cartridge 16 to take multiple conductance measurements simultaneously.

Additional aspects of one of the conductance sensor devices 38 are described below. It should be understood that each of the conductance sensor devices 38 on the cartridge 16 may be the same or similar to the conductance sensor device 38. The conductance sensor device 38 may be electrically coupled to a power source in the handle 14, such as an internal battery, via one or more electrically-conductive wires and/or contacts. In one aspect, an alternating current voltage may be applied across the first and second electrodes 40 and 42, and the conductance sensor device 38 may measure an electrical resistance of the portion of the user's skin between the first and second electrodes 40 and 42. The electrical resistance may provide an indication of the physical composition of the user's skin. The conductance of the user's skin may be determined based on the resistance because the conductance is the reciprocal of the resistance. In some aspects, conductance measurements may be made once prior to and/or during a shaving session, repeatedly at one or more time intervals during a shaving session, or continuously during a shaving session or even after a shaving session.

The first and second electrodes 40 and 42 may be made of any suitable material including, for example, stainless steel, copper, graphite, titanium, brass, silver, and platinum, depending on the desired conductance, corrosion resistance, hardness, current load, form, and size of the electrodes 40 and 42. The first and second electrodes 40 and 42 may be plate electrodes, transformer coils, and/or may take any other suitable form. In some embodiments, electrodes 40 and 42 may be relatively flush with the surface of cartridge 16. In other embodiments, electrodes 40 and 42 may form atraumatic protrusions on the surface of cartridge 16.

The shaver 12 may include or may be otherwise coupled to one or more processor(s) 46 in operative communication with the conductance sensor device 38. The processor(s) 46 may be in the handle 14 or in external components, such as the base 18, the user device 20, and/or the merchant unit 22. The processor(s) 46 may include an analog to digital converter to convert analog signals from the conductance sensor device 38 into digital signals for processing. The processor(s) 46 may be equipped with software configured to analyze the data (e.g., conductance measurements) to identify the user's skin characteristics and/or make suggestions based thereon. It is contemplated that one or more of the other exemplary sensor devices (e.g., the sensor devices in the handle 14 and/or the cartridge 16, described in detail in the paragraphs below) may include the conductance sensor device 38.

In another example, one or more of the sensor devices may include a temperature sensor 47 that may contact the user's skin, such as a resistance temperature detector, a thermocouple, and/or a thermistor (FIG. 5). These types of sensor devices may be placed in contact with the user's skin during a shaving session. One way of sensing a skin characteristic like skin irritation may include measuring a temperature of a user's skin and/or a change in the temperature of the user's skin, before, during, and/or after a shaving session. The measured temperature of a user's skin may be influenced by a multitude of factors. A user's skin contains a multitude of blood vessels. When areas of the skin are injured during a shaving session (e.g., scraped, scratched, nicked, cut, or otherwise damaged), blood may rush to the afflicted areas via those blood vessels. The rush of blood may transport heat to the afflicted areas, leading to an increase in the temperature of those areas.

It also is contemplated that the sensor device 47 may include a sensor that remotely senses one or more characteristics of the user's skin. Such sensor devices may include electro-optical sensors. These sensor devices may be configured to measure characteristics of the user's skin regardless of whether the sensor device 47 is in direct contact with the user's skin. Such a sensor device may measure the temperature of the user's skin. Additionally or alternatively, such a sensor device may provide information about characteristics associated with the user's skin other than temperature. For example, the sensor device 47 may measure the color of the user's skin to detect a change of color resulting from a change in blood flow or concentration of blood in the user's skin, which may be indicative of skin irritation. In another example, the sensor devices 47 may measure blood pressure in the user's skin via monitoring of the skin to detect changes in pressure that may be indicative of skin irritation. For example, flushed skin may be indicative of relatively higher blood pressure resulting from an increase in blood flow to a damaged or otherwise irritated skin area.

One or more of the sensor devices 47 may be positioned on surfaces of the cartridge 16 that face and/or contact the user's skin during a shaving session (see FIG. 5). For example, one or more of the sensor devices 47 may be on one or more peripheral portions of the cartridge 16 that surround the blades 34 (e.g., on one or more clips 44 holding the blades 34 on the cartridge 16, and/or on one or more portions of the cartridge that extend adjacent the blades 34 along the longitudinal direction of the blades 34). Positioning the sensor devices 47 in these locations may be suitable for the sensor devices that sense via contact with the user's skin, since the locations tend to come into contact with the user's skin during a shaving session. The positioning also is suitable for sensor devices that sense remotely (e.g., without direct contact with the user's skin), because such sensor devices may nevertheless have line of sight to the user's skin.

It also is contemplated that one or more of the sensor devices 47 may be positioned on other surfaces of the shaver 12. For example, one or more of the sensor devices 47 may be positioned on one or more lateral wall portions of the cartridge 16, within the cartridge 16, on the handle 14, and/or within the handle 14. Additionally or alternatively, one or more of the sensors 36 may be positioned on a surface of the cartridge 16 behind the blades 34. These locations may be suitable for sensor devices that sense remotely (e.g., without direct contact with the user's skin) if the sensor devices have line of sight to the user's skin from whatever surface the sensor devices may be on, including line of sight to the user's skin through gaps between the blades 34 and/or other cartridge structures.

Additional aspects of one remote or electro-optical sensor device 47 are described below. The sensor device 47 may be electrically coupled to a power source in the handle 14, such as an internal battery, via one or more electrically-conductive wires and/or contacts.

In one aspect, the electro-optical sensor device 47 may include a light source and a receiver. The light source may emit light onto the user's skin. The light source may include a light emitting diode (LED), such as a red light emitting LED, a green light emitting LED, an infrared radiation emitting LED, or any other suitable light emitter, LED or otherwise. The user's skin may reflect at least some of the light, and the receiver may receive the reflected light. The user can take a "snapshot" of his or her skin tone before shaving, so that the shaver 12 can have a baseline measurement of the user's skin tone and sense irritations/redness accordingly. The degree to which the user's skin reflects the light may be a function of the tone or color of the user's skin, which may be indicative of blood concentration in the user's skin and/or blood pressure in the user's skin. The user's skin may have one light reflectance value when the user's skin is not irritated, and a different light reflectance value when the user's skin is irritated. Moreover, the light reflectance value may vary based on the degree to which the user's skin is irritated. Accordingly, the sensor device 47 may identify and/or quantify skin irritation by monitoring the light reflectance of the user's skin. The sensor device 47 may output an electrical signal indicative of one or more characteristics of the reflected light received by the receiver.

In another aspect, the electro-optical sensor device 47 may include a lens that may focus infrared thermal radiation emitted by the user's skin to a detector. The sensor device 47 need not include a light source for emitting light onto the user's skin, but a light source may be included to assist with detection, if desired. The degree to which the user's skin emits infrared thermal radiation may be a function of the blood concentration in the user's skin and/or blood pressure in the user's skin. The user's skin may emit infrared thermal radiation at one level when the user's skin is not irritated, and at a different level when the user's skin is irritated. Moreover, the level of infrared thermal radiation may vary based on the degree to which the user's skin is irritated. Accordingly, the sensor device 47 may identify and/or quantify skin irritation by monitoring the infrared thermal radiation of the user's skin. The sensor device 47 may output an electrical signal indicative of one or more characteristics of the infrared thermal radiation detected by the detector.

It is contemplated that the shaver 12 may include or may be otherwise coupled to one or more processor(s) 46 in operative communication with the sensor device(s) 47. The processor(s) 46 may be equipped with software configured to analyze the data (e.g., temperature, color, blood pressure, and/or blood concentration measurements) to identify and quantify skin characteristics (e.g., skin irritation) and/or make suggestions based thereon. It is contemplated that one or more of the other exemplary sensor devices (e.g., the sensor devices in the handle 14 and/or the cartridge 16, described in detail in the paragraphs below) may include the sensor device 47.

When multiple sensor devices are used in the shaver 12, the sensor devices may be configured to detect different regions of the user's skin. For example, one sensor device may be directed at a region of the user's skin that is going to be shaved (e.g., at or near a leading edge of the shaver 12), while another sensor device may be directed at a region of the user's skin that has been shaved (e.g., at or near a trailing edge of the shaver 12). A comparison of readings from the sensor devices may provide an indication of the level of skin irritation that has resulted from a shaving stroke. It also is contemplated that different types of sensor devices (e.g., the types described in the paragraphs above and below) may be used simultaneously. Thus, to the extent one type of sensor device is more adept at sensing skin temperature, another type of sensor device is more adept at sensing skin color, another type of sensor device is more adept at sensing blood pressure, another type of sensor device is more adept at sensing blood concentration, another type of sensor device is more adept at sensing skin conductance, and another type of sensor device is more adept at sensing skin elasticity, a combination of sensor devices of different types may be used simultaneously to provide multiple means of sensing skin characteristics, for greater accuracy and/or precision.

According to another aspect of the present disclosure, and as shown in FIGS. 6 and 7 and discussed in more detail below, a sensor device 48 may include an open recess, lumen, or cavity 50, a suction source 52, a light source 54, and a light detector 56. The sensor device 48 may be incorporated into the handle body 30, on an opposite end from the handle attachment interface 32. In one example, the suction source 52, light source 54, and light detector 56 may be incorporated on or within the cavity 50. The cavity 50 may be positioned at a proximal portion of the handle 14, and the handle attachment interface 32 may be positioned on a distal portion of the handle 14. Alternatively, the sensor device 48 may be included on an element separate from the handle body 30 configured to attach and detach from handle 14 and may be releasably couplable to the handle body 30. As mentioned above, the sensor device 48 may be operated by a user via a button or switch (not shown), which may be positioned on the handle 14 or the base 18, or alternatively, the sensor device 48 may be controlled by the user device 20 or another remote device. As discussed in more detail below, the sensor device 48 may be operably coupled to or include a processor (not shown) similar to the processor 46. For example, the processor may have software and/or one or more algorithms stored thereon that are configured to receive and analyze raw sensor data. The sensor assembly 48 or handle 14 may further include a power source and a communication unit, such that data or other signals may be transmitted to, and from, one or more of the base 18, the user device 20, or a merchant unit 22. In one example, sensor device 48 may include a Cutometer® sensor marketed by Courage+Khazaka electronic GmbH.

FIGS. 6 and 7 illustrate cross-sectional views of aspects of the proximal portion of handle 14 that may be used to measure a characteristic, such as skin elasticity, of a user's skin. In one aspect, the end of the handle body 30 may be pressed against the user's skin 58 to at least partially deform the skin 58. The suction source 52 may be configured to apply negative pressure at the open end of the cavity 50, which may be positioned on or adjacent to the user's skin 58. Hence, one or more upper skin layers 60, for example, the epidermis, may be drawn into the cavity 50. Although not shown, the suction source 52 may include a negative pressure pump with an outlet. The negative pressure pump may be positioned anywhere within (or operably coupled to) the handle body 30, and the outlet may be positioned anywhere on the handle body 30, for example, on the distal portion, to allow withdrawn air to flow out of the negative pressure pump and out of the handle body 30.

The light source 54 may emit light, which may then be detected by the light detector 56. In some aspects, the light source 54 may emit light at wavelengths that are not harmful to skin, for example, visible light at a low intensity so as to not generate harmful heat. The light detector 56 may be positioned opposite to the light source 54, and may detect light from the light source 54 that traverses the cavity 50. In one aspect, the light source 54 and the light detector 56 may each include a prism, and the prisms may direct the light from the light source 54 to the light detector 56. Furthermore, an intensity and/or amount of light detected by the light detector 56 may vary based on if and how much tissue of the user's skin is drawn into the cavity 50 when the suction source 52 applies suction. Each of the suction source 52, light source 54, and light detector 56 may be battery powered with a battery contained within the handle body 30, or may be powered by an external power source, for example, through a wired connection with the base 18 or a household electrical outlet.

With the suction source 52 activated, the drawn portion 60 of the skin 58 may be at least partially between the light source 54 and the light detector 56, thereby at least partially obstructing the path of light rays traveling from the light source 54 to the light detector 56. As a result, the light detector 56 may detect a lesser amount of light than without the drawn portion 60 drawn into the cavity 50 by the suction source 20. Different types of skin 58 may be withdrawn into the cavity 60 to differing extents, even with a constant amount of negative pressure (or vacuum force) from the suction source 52. Hence, based on the applied negative pressure from the suction source 52 and the amount of light detected by the light detector 56, the sensor device 48 may be configured to facilitate the determination of the elasticity of the skin 58.

The sensor device 48 may transmit measured information indicative of skin elasticity to the base 18, the user device 20, and/or the merchant device 22. Based on the determined skin elasticity, and any additional user information, the base 18, the user device 20, and/or the merchant device 22 may recommend a particular type of cartridge 16 and/or a configuration of razor blades 34. Alternatively, the handle 14 may include a display and/or light indicator that may indicate that a particular cartridge 16 coupled to the handle 14 is appropriate or inappropriate for the user's skin 58, based on the determined skin elasticity.

FIG. 9 illustrates how the skin 58 may react during a shaving session. For example, the cartridge 16 may include five razor blades 34 equally spaced apart, and portions 59 of the skin 58 that are between the razor blades 34 may protrude upward toward the cartridge 16 (and in between adjacent blades 34) as the cartridge 16 is pressed against and moves across the skin 58. If the skin 58 has relatively high skin elasticity, then the portions 59 of the skin 58 that are between the razor blades 34 may be wide and/or protrude toward the cartridge 16. As such, there may be an increased likelihood of a cut, nick, irritation, or other skin trauma during the shaving session. However, if the skin 58 has relatively low skin elasticity, then the portions 59 of the skin 58 that are between the razor blades 34 may be narrow and/or not protrude very far toward the cartridge 16 and into the area in between adjacent blades 34. As such, there may be less of a likelihood of a cut, nick, irritation, or other skin trauma during the shaving session.

Based on this correlation between the skin elasticity of a user's skin 58 and the comfort and/or ease of a shaving session, the system 10 may recommend a cartridge 16 with a particular configuration of the razor blades 34 to suit a user based on the information from the sensor device 48. For example, if the skin elasticity of the user's skin 58 is relatively high, the system 10 may recommend a cartridge 16 with a greater number of razor blades 34 spaced relatively closely together, which may reduce the likelihood of cuts, nicks, irritations, and other skin trauma that may result from a shaving session. Alternatively, if the skin elasticity of the user's skin 58 is relatively low, then the system 10 may recommend a cartridge 16 with fewer razor blades 34 with relatively more space between each razor blade 34, as the user may not benefit from a greater number of razor blades 34 spaced relatively closely together. The cartridges with a greater number of razor blades 34 may also be more expensive than the cartridges with fewer razor blades 34, so the system 10 may recommend the most appropriate and cost-effective cartridge 16 for the user. The aforementioned recommendations may also be based on other input information, such as, for example, skin characteristics, skin sensitivity and/or dryness, frequency of shaving sessions, the area of skin 58 the user is shaving, skin irritation, and other user preferences or information.

In a further aspect, a sensor device 62 may be coupled to the razor blades 34 in the cartridge 16 (see FIG. 8). In this aspect, the razor blades 34 may be coupled to razor springs 64, with the razor springs 64 coupled to the razor blades 34 on the side of the razor blades 34 that do not contact the skin 40. The razor springs 64, in turn, may be coupled to the sensor device 62, which may include a strain gauge, a pressure sensor, an optical sensor, a displacement sensor, a proximity sensor, and/or any other suitable sensor. A user may press the razor blades 34 against the portion of the skin to be shaved, but not move the razor blades 34 along the surface of the skin. Based on any deformation and/or flexion of the razor springs 64, the sensor device 62 may measure skin elasticity for the portion of the skin. As discussed above, the system 10 may confirm that the cartridge 16 includes an appropriate configuration of the razor blades 34 for the skin of the user, or the system 10 may recommend a cartridge with a different configuration of the razor blades 34 that may provide for a more comfortable shaving session for the user.

In some aspects, a test cartridge may be provided, wherein the test cartridge includes a plurality of spring fingers in the place of razor blades 34. A user may use such a test cartridge to determine skin elasticity, and whether a particular blade number, configuration, or spacing is optimal for the user's skin, based on the determined skin elasticity. Furthermore, such a test cartridge may be included in a dispenser with a variety of cartridges, where each of the cartridges includes a different configuration of razor blades 34. As such, the user may use the test cartridge to determine skin elasticity and, based on whether a particular blade number, configuration, or spacing is optimal for the user's skin, the user may use a particular cartridge from the dispenser.

It is noted that the skin on different portions of a user's body may exhibit differing skin elasticities. Therefore, the system 10 may recommend one cartridge for a user shaving a face, and may recommend a different cartridge for a user shaving a leg or other portion of the body.

Figure 10:
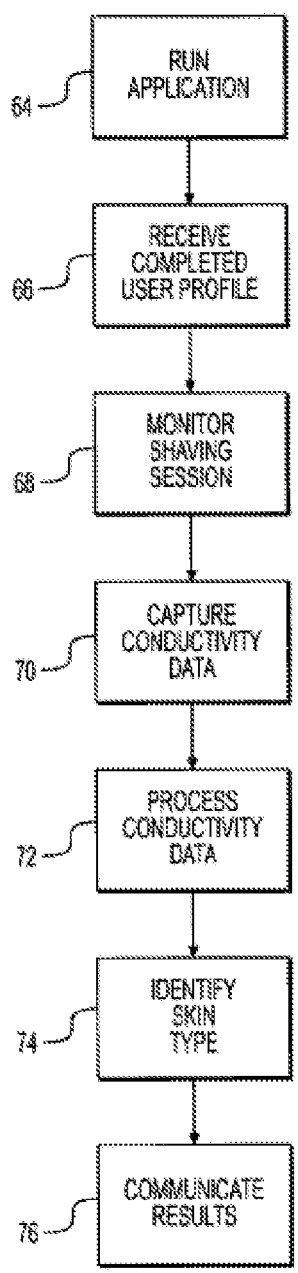
FIG. 10 depicts a flow diagram of a method for determining a skin characteristics, according to aspects of the present disclosure.

As described in the paragraphs above, the system 10 may facilitate the performance of methods for improving the shaving experience. For example, as depicted in FIG. 10, in use, a user may download an application run by the processor(s) 46 (step 64). Instead of downloading the application, the user may access the application via, e.g., a website on the Internet. The user may complete a user profile for the application (step 66). The user profile may include identifying information about the user, products the user uses for shaving sessions, shaving techniques used by the user, user preferences, and information about the user's skin and/or skincare habits. With that information in place, the user may carry out a shaving session (step 68).

During the shaving session, skin conductance data may be captured by the conductance sensor device(s) 38 (step 70). In some aspects, however, the application may prompt the user to make one or more conductance measurements prior to a shaving session. For example, the user may be prompted to touch the cartridge 16 to one or more locations on the user's skin without application of a shaving agent or water. Such pre-shave measurements may provide "baseline" conductance measurements. Additionally or alternatively, a user may be prompted to make one or more conductance measurements after a shaving session. These results can then be combined with the "baseline" conductance measurements to determine skin characteristics even more accurately but also skin behavior after a shaving session. Any of the sensor devices described in the paragraphs above, including sensor devices on the cartridge 16, in the cartridge 16, and/or in the handle 14, may be configured for taking conductance measurements.

The data captured by the conductance sensor device(s) 38 may be analyzed by the processor(s) 46 (step 72). The processor(s) 46 may identify the user's skin characteristics based on the captured data, the analysis of the data, and/or the user inputs/profile (step 74). For example, the user's skin may be categorized based on comparing the measured conductance of the user's skin to one or more threshold ranges or values associated with one or more skin characteristics categories. Examples of skin characteristics categories include normal skin, dry skin, oily skin, combination skin, sensitive skin, mature skin, and/or any other category. Results of the analysis may be communicated to the user and/or any of the components of the shaving system 10 (step 76).

Normal skin may include skin that has a relatively smooth texture and a rosy, clear surface, with fine pores. Normal skin may have few or no visible blemishes, greasy patches or flaky areas. With normal skin, sebum production, moisture content, keratinisation and desquamation may be well-balanced. Dry skin may lack moisture in its corneous layer, resulting in tightness and/or flaking. Dry skin may appear dull, and/or may lack elasticity, with accentuated fine lines and wrinkles. In more severe cases, itching and burning may occur. Extremely dry skin may show signs of cracking and fissuring. Oily skin may include a relatively high amount of lipids on the skin surface due to overactive sebaceous glands. It may be shiny and thick, often with enlarged pores. Combination skin may be dry in some parts of the body and oily in other localizations. Sensitive skin may react with redness, itching, burning, or dryness when agitated by, for example, shaving. With mature skin, the skin's sebum production may have slowed down, often leading to increased dryness, an accentuation of fine lines and wrinkles, and flakiness. The skin may appear dull, and/or may itch and burn.

Figure 11:
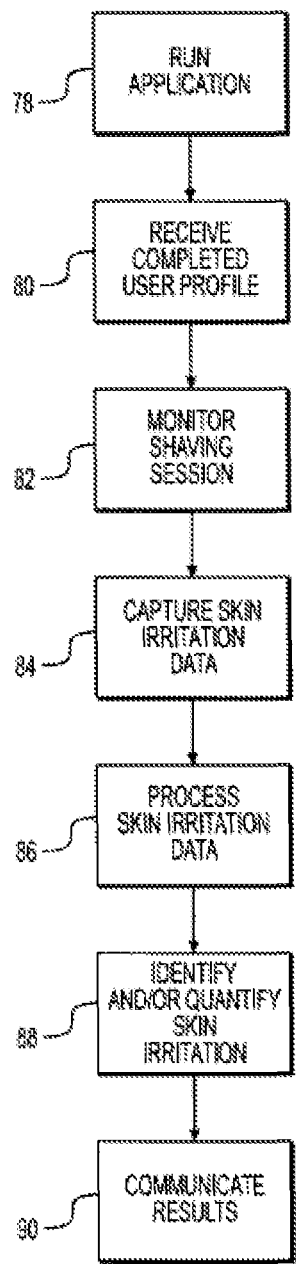
FIG. 11 depicts a flow diagram of a method for determining skin irritation, according to aspects of the present disclosure.

Additionally or alternatively, as depicted in FIG. 11, a method of use is shown with steps 78, 80, and 82, similar to steps 64, 66, and 68 of FIG. 10. In this method, the user profile may include a "snapshot" of the user's skin tone before shaving, the "snapshot" being taken by the sensor device(s) 47 and/or the user device 20, so that the shaving system 10, including the processor(s) 46, can have a baseline measurement of the user's skin tone and sense irritations/redness accordingly.

During the shaving session, skin irritation data may be captured by the one or more sensor devices 47 (step 84). In some aspects, however, the application may prompt the user to make one or more measurements prior to a shaving session. For example, the user may be prompted to bring the shaver 12 near to or in contact with one or more locations on the user's skin without application of a shaving agent or water. Such pre-shave measurements may provide "baseline" measurements from which a level of skin irritation caused by shaving may be determined. One type of baseline measurement includes the aforementioned "snapshots." A user may also be prompted to make one or more measurements after a shaving session. These results can then be combined with the "baseline" measurements to determine skin behavior (e.g., irritation) after a shaving session. Any of the sensor devices described in the paragraphs above, including sensor devices on the cartridge 16, in the cartridge 16, and/or in the handle 14, may be configured for taking skin irritation measurements.

The data captured by the sensor device(s) 47 may be analyzed by the processor(s) 46 (step 86). The processor(s) 46 may identify and/or quantify skin irritation based on the captured data, the analysis of the data, and/or the user inputs/profile (step 88). For example, skin irritation may be identified and/or quantified based on comparing the measured skin temperature, color, blood concentration, and/or blood pressure to one or more threshold ranges or values indicative of skin irritation and/or lack thereof. Results of the analysis may be communicated to the user and/or any of the components of the shaving system 10 (step 90).

The results of the analysis may be communicated in any suitable form. The results may be communicated in the form of an audio and/or visual alert on the display 30. Additionally or alternatively, the skin irritation data from the shaver 12 may be analyzed in conjunction with images of the user or information about the user captured before a shaving session. For example, before shaving takes place, the user may download an application on his or her smartphone or computer, or access a website with the same functionality as the application. The user may be prompted to take or upload one or more photographs or videos of the relevant body part to be shaved. The camera device used to capture user images may be the camera built into or connected to a smartphone or computer, or a separate camera, from which the images may be downloaded and then uploaded via a hard or wireless connection.

The photographic information may be stored in a database, and, based on the photographic information, a three-dimensional (3-D) model of the user's body part may be generated. In some embodiments, particular landmarks and/or digital flag posts may be generated corresponding to anatomical features. In some embodiments, the body region photographed may be broken up into shaving regions. For example, a user may define which areas of the body region are to be shaved, or the application may automatically break the image up into regions that represent the average shaving patterns of people generally or of that particular user. As the user shaves, skin irritation information may be analyzed in conjunction with the images, 3-D model, and/or shaving regions in order to provide feedback to the user as to where skin irritation has been detected. The shaver 12 may include a global positioning system or similar device that may help determine the location of the shaver 12 relative to the user's anatomy, its orientation, and/or its path of travel along the user's skin, which may facilitate arrangement of the skin irritation data on the 3-D model. It also is contemplated that skin conductance and/or skin elasticity may be tracked and modeled in a similar manner.

Figure 12:
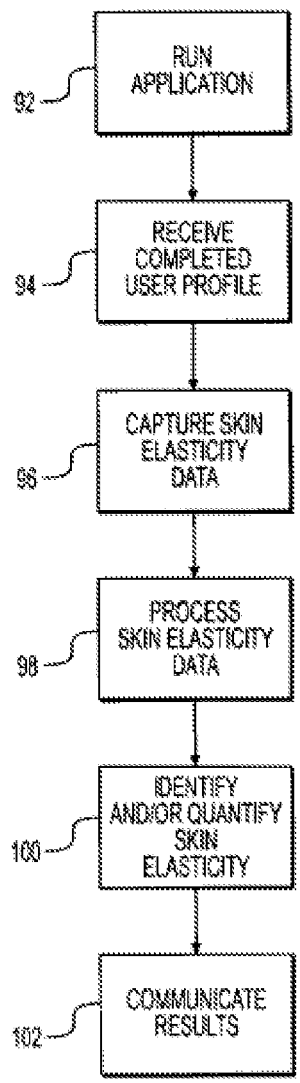
FIG. 12 is a flow diagram of a method for determining skin elasticity, according to aspects of the present disclosure.

Additionally or alternatively, as depicted in FIG. 12, a method of use is shown with steps 92 and 94, similar to steps 64 and 66 of FIG. 10. Before, during, and/or after a shaving session, skin elasticity data may be captured by the sensor device 48 (step 96). For example, in some aspects, however, the application may prompt the user to make one or more measurements prior to a shaving session. The user may be prompted to bring the shaver 12 near to or in contact with one or more locations on the user's skin. This may be performed without application of a shaving agent or water. Any of the sensor devices described in the paragraphs above, including sensor devices on the cartridge 16, in the cartridge 16, and/or in the handle 14, may be configured for taking skin elasticity measurements.

As part of step 96, the open end of the cavity 50 may be positioned adjacent to an area of the user's skin, and the suction source 52 may apply negative pressure to draw a portion of the skin into the cavity 50. The light source 54 may emit light, and based on the amount of light received by the light detector 56, the sensor assembly 48 may measure the skin elasticity of that area of the skin. Specifically, the light received by the light detector 56 may be communicated to a processor (e.g., processor 46) (step 98) for determining the skin elasticity (step 100). The system 10 may also prompt the user, via the handle 14, the base 18, and/or the user device 20, to repeat the skin elasticity measurement, perform the skin elasticity measurement on a different portion of the skin, or to perform another operation. Alternatively, the sensor assembly 62 may be provided on/in the cartridge 16, as described above. Results of the analysis may be communicated to the user and/or any of the components of the shaving system 10 (step 102).

Turning to FIG. 13, the processor(s) 46 may be configured to determine whether the user would benefit from one or more specialized items (e.g., shaving cartridges optimized for sensitive skin) or techniques to optimize shaving performance and comfort. For example, after performing steps 76, 90, or 102, or as part of performing steps 76, 90, or 102, the processor(s) 46 may recommend shaving products (e.g., shavers, lubricants, moisturizers, cartridges with differing blade types and arrangements such as blade spacing and exposures, etc.), shaving techniques, and/or treatment regimens to the user (step 104) based on the user's skin characteristics, skin irritation, or skin elasticity. The recommendations may be communicated to the user via any suitable display of the shaving system 10. The user may order the recommended shaving products and/or treatment regimens from one or more merchants using any suitable input means of the system 10, by communicating with the merchant unit(s) 22 of the system 10 through, for example, the downloaded application (step 106). Additionally or alternatively, the recommended shaving products and/or treatment regimens may be automatically ordered by the application. During subsequent shaving sessions, the effectiveness of the recommendations may be tracked by measuring the conductance of the user's skin, irritation of the user's skin, or elasticity of the user's skin, and looking for changes in the measured values (step 108). Additional or alternatively recommendations may be made based on the results of the tracking (step 110).

Additionally or alternatively, the processor(s) 46 may compare data captured during one or more shaving sessions performed by the user with a first shave product (e.g., a first lubricant or blade cartridge) with data captured during one or more other shaving sessions performed by the user with a second shave product (e.g., a second lubricant or blade cartridge) to identify differences in the conductance, irritation, or elasticity measurements of the user's skin between the sessions. The processor(s) 46 may make suggestions based on the existence or extent of differences in conductance, irritation, or elasticity. For example, if a change in conductance, irritation, or elasticity indicates that characteristics of the user's skin have fallen outside a desirable range or ranges, the processor(s) 46 may make suggestions to the user to return the characteristics back into the desirable range/ranges. The processor(s) 46 may use one or more shaving sessions to calibrate the system 10, for use as a starting point against which future shaving sessions may be compared, thus eliminating variables between shaving sessions and/or facilitating tracking of the progress of treatments and/or other interventions. In this example, the step of assigning the user's skin characteristics to a predetermined category may be bypassed or omitted.

In some aspects, a cartridge may include adjustable configurations or geometries of the razor blades 34. For example, the cartridge may include a dial, lever, screw, or other input device directly or indirectly coupled to razor blades 34, e.g., via a magnet, that allows a user to adjust a spacing between and/or an angle of the razor blades 34. The system 10 may recommend a particular spacing or angle of the razor blades 34 to the user based on the information from the sensor device(s) (e.g., the sensor device 48 and/or the other sensor devices described above), and the user may accordingly adjust the spacing or angle of the razor blades 34 before beginning a shaving session.

Moreover, a cartridge may be packaged and/or distributed in a dispenser, where the dispenser includes different cartridges, with each cartridge in the dispenser including one or more of a different blade number, blade spacing, blade geometry, angle, coating, thickness, etc. The cartridges may further include identification indicators, such as, for example, radio-frequency identifiers, barcodes, QR codes, model numbers, serial numbers, or other indicators that may be read by or input into one or more of the sensor devices (e.g., the sensor device 48 or the other sensor devices described above), base 18, and/or user device 20. For example, a user may scan a QR code for a cartridge with a camera incorporated into the user device 20. Based on the identification of the cartridge and/or the reading from the sensor device (e.g., the sensor device 48 and/or the other sensor devices described above), at least one of the sensor devices, base 18, user device 20, and/or merchant device 22 may indicate to a user whether the cartridge 16 includes an appropriate blade geometry for the user, may recommend a particular shaving technique, and/or may recommend a cartridge with a different configuration of the razor blades 34, for example, a different cartridge in the dispenser.

In another example, a cartridge may include multiple geometries or configurations of razor blades 34 within the same cartridge. For instance, the cartridge may include two or three shaving surfaces or sides, with each shaving surface including a different number or configuration of razor blades 34. The shaving surface may be configured such that the cartridge may be attached to a handle 14 as discussed above, and a user may shave his or her skin with one or more of the shaving surfaces. For example, based on the information obtained by the sensor device(s) (e.g., the sensor device 48 and/or the other sensor devices described above), the system 10 may recommend a particular shaving surface for the skin of the user with a reduced likelihood of cuts, nicks, irritations, or other skin trauma. Alternatively or additionally, a user may try shaving with each of the shaving surfaces, and may determine which shaving surface the user prefers in light of the recommendation from the system 10 and/or an estimated cost of the various types of cartridges.

Additionally or alternatively, FIG. 14 shows a process that may be performed in place of, as part of, or in addition to the process in FIG. 13. For example, steps 104 and 106 (FIG. 13) may involve the system 10 providing a recommended cartridge 16 and/or configuration of razor blades 34 (step 112). The system 10 may identify the cartridge 16 coupled to the handle 14. The system 10, via the handle 14, the base 18, or the user device 20, may confirm that the cartridge 16 coupled to the handle 14 is an appropriate cartridge for the skin of the user based, e.g., on the conductance, irritation, and/or elasticity of the user's skin. Alternatively, the system 10, via the handle 14, the base 18, or the user device 20, may recommend a particular cartridge 16 and/or configuration of razor blades 34 for the skin of the user. Furthermore, if the cartridge 16 includes adjustable razor blades 34, the system 10 may recommend a particular blade configuration, blade number, blade spacing, and/or blade geometry that a user may input or adjust on the cartridge 16.

In step 114, the system 10 may prompt a user to initiate or confirm an order for the recommended cartridge(s) and/or a configuration of razor blades. For example, the system 10 may display the recommended cartridge 16 and/or configuration of razor blades 34. The system 10 may identify the cartridge 16 currently coupled to the handle 14, and/or identify the cartridges 16 within a proximity or within the user's inventory based on the aforementioned identification steps or based on a user's previously input inventory. If the cartridge 16 currently coupled to the handle 14 is recommended for the skin of the user, the system 10 may provide the user with an indication to begin the shaving session, including suggestions for the shaving session. If the cartridge 16 currently coupled to the handle 14 is not recommended for the skin of the user and the user does not have the recommended cartridge 16 at his or her disposal, the system 10 may provide the user with the option to initiate or confirm an order from a merchant unit 22 for one or more of the recommended cartridge(s) 16, for example, a dispenser including a plurality of the recommended cartridges 16. Furthermore, the system 10 may provide the user with the option to purchase additional items, such as, for example, shaving cream, aftershave lotion, moisturizer, additional handles, and other shaving or skincare accessories. Alternatively, the order may be automatically placed by system 10 or may be based on pre-selected user preferences. The system 10 may further track the user selections and/or purchases and incorporate the selections in further prompts and orders.

It is noted that additional aspects may be incorporated in any of the elements and systems discussed above. For example, the system 10 may allow the user to track his or her skin conductance, skin irritation, or skin elasticity, for example, if the user loses weight or is using a skin toning treatment. The system 10 may prompt the user to measure his or her skin periodically, for example, once a month, and may display the information from the sensor device(s) on the base 18 and/or the user device 20. The base 18 and/or the user device 20 may also provide the user with shaving tips and/or recommendations based on the measured skin properties of the user, the user's preferences, the user's shaving frequency, the portion of the user's body that the user is shaving, the user's hair and body type, etc. The user's hair and body type may be monitored by elements coupled to the cartridge 16 and/or handle 14, such as, for example, a camera or other sensing element.

Furthermore, the base 18 and/or user device 20 may include a camera or additional sensing elements that allow the system 10 to obtain user data by, for example, taking a picture of the portion of the user's skin before, during, and/or after a shaving session. If a cartridge 16 has been used more than the recommended number of usages, the base 18 may produce an audible or a visible notification to indicate to the user that he or she should replace the cartridge 16. This notification may also be sent to the user device 20. This notification may appear on the display 30 of the base 18, may be a flashing light, or any other indication. The base 18 may include a manual reset to override the cartridge usage notification. The notification may also be based on the number of user strokes detected by a stroke sensing element coupled to or a part of the cartridge 16 or handle 14, in addition to number of usages. For example, if a user is only trimming the edges of a beard, the user may use fewer strokes, and thus the cartridge 16 may have a higher recommended number of usages than if the user was shaving a face or legs and using a greater number of strokes.

The system 10 and related methods may provide a user with a recommendation for a cartridge 16 having a configuration of razor blades 34 most likely to provide a user with a comfortable shaving experience. As a result, the user may achieve a comfortable shave during a shaving session, with a reduced likelihood of cuts, nicks, irritations, or other skin trauma. Furthermore, with the sensor device(s) coupled to the handle 14 or the cartridge 16, the user may conveniently measure the conductance, irritation, and/or elasticity of the portion of the skin to shave. If the user has previously measured the skin conductance, irritation, and/or elasticity and the user's skin may have changed based on, for example, age, weight, sun exposure, etc., the user may easily confirm that the previously indicated cartridge 16 is still appropriate for the user's skin, or the system 10 may recommend a different cartridge 16 or configuration of razor blades 34 for the user based on additional measurements made according to the principles described above. The system 10 may also allow the user to easily place orders for cartridge 16, for example, replacement orders.

The disclosed system 10 and related methods also may provide a merchant the ability to track user skin conductance, irritation, and/or elasticities, cartridge and blade geometry recommendations, cartridge usage, purchasing patterns, and/or other user information. For example, the system 10 and related methods may be used and performed by a plurality of users, with each sensor device of each system 10 operably coupled a communication unit in the handle 14, base 18, and/or user device 20. The communication unit may transmit user data to a merchant database or to a database to which a merchant has access. The user data may be stored, accumulated, and/or processed within the database. The merchant may then access the user data in the database to determine average skin conductance, irritation, and/or elasticities, common cartridge and blade geometry recommendations, average cartridge usage, common purchasing patterns, and other user information. The user data may also be filterable and/or sortable by, for example, region, age, ethnicity, gender, and other demographic information. Based on this user data, the merchant may then provide targeted advertisements or offers to select users, or to other potential consumers in particular areas, age ranges, demographics, etc. Additionally, it is understood that the systems and methods disclosed herein may be applied to various other applications as well.

The many features and advantages of the present disclosure are apparent from the detailed specification, and thus, it is intended by the appended claims to cover all such features and advantages of the present disclosure that fall within the true spirit and scope of the disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

Technical and scientific terms used herein have the same meaning as commonly understood to one of ordinary skill in the art to which this disclosure belongs unless clearly indicated otherwise. As used herein the singular forms "a", "an", and "the" include plural references unless the context clearly dictates otherwise. Thus, for example, reference to "a sensor" may include a plurality of such sensors and reference to "the sensor" may include reference to one or more sensors and equivalents thereof known to those skilled in the art, and so forth.

The above description is illustrative, and is not intended to be restrictive. One of ordinary skill in the art may make numerous modification and/or changes without departing from the general scope of the disclosure. For example, and as has been described, the above-described embodiments (and/or aspects thereof) may be used in combination with each other. Additionally, portions of the above-described embodiments may be removed without departing from the scope of the disclosure. In addition, modifications may be made to adapt a particular situation or material to the teachings of the various embodiments without departing from their scope. Many other embodiments will also be apparent to those of skill in the art upon reviewing the above description.

What is claimed is:

1. A shaver system, comprising:
   a base with a processor;
   a handle body extending from a first end to a second end;
   a cartridge coupled to the second end of the handle body, the cartridge including a plurality of razor blades; and
   a skin elasticity sensor located within the handle body, wherein the skin elasticity sensor includes a suction source, a light source, and a light detector, and wherein the skin elasticity sensor transmits measured information indicative of skin elasticity of a user from the skin elasticity sensor to the processor,
   which the processor generates a blade geometry recommendation that includes a recommendation to use a first configuration, based on a first skin elasticity sensor measurement, and to use a second different configuration, based on a second different elasticity sensor measurement, wherein the first configuration includes a first number of razor blades and a first spacing between the first number of razor blades and the second configuration includes a second different number of razor blades and a second spacing distance between the second number of razor blades.

2. The shaver system of claim 1, wherein the handle body includes a cartridge attachment portion; and
   wherein the skin elasticity sensor is positioned in a portion of the handle body opposite to the cartridge attachment portion.

3. The shaver system of claim 1, wherein the skin elasticity sensor is configured to be positioned adjacent to a user's skin.

4. The shaver system of claim 1, the handle body further including a cavity located in a terminal portion at the first end of the handle body, wherein the cavity including an opening, a circumferential edge that surrounds the opening, and a recessed inner wall including an inner chamber.

5. The shaver system of claim 4, wherein the light detector and the light source are positioned on opposite sides of the circumferential edge of the cavity,
   wherein the suction source is configured to apply a negative pressure to the cavity and is located within the inner chamber of the recessed inner wall and spaced away from the light detector and the light source, such that the skin of the user that is near or adjacent to the cavity is drawn into the cavity by the negative pressure of the suction source, the light source emits a known amount of light through the skin of the user within the cavity, and the light detector measures an amount of detected light that passes through the skin of the user, wherein the measured information indicative of the skin elasticity of the user, including an amount of negative pressure applied and the amount of detected light, is provided to the skin elasticity sensor.

6. The shaver system of claim 5, wherein the inner chamber has a smaller diameter than the circumferential edge.

7. The shaver system of claim 1, wherein at least one spring coupled to the plurality of razor blades is configured to deform relative to the skin of the user, thereby providing the skin elasticity sensor with a deformation measurement for the skin elasticity of a portion of skin of the user.

* * * * *